(12) United States Patent
Koppel et al.

(10) Patent No.: US 10,590,349 B2
(45) Date of Patent: Mar. 17, 2020

(54) PROCESSING OF GASIFICATION TARS TO HIGH YIELDS OF BTX

(71) Applicant: Fluor Technologies Corporation, Sugar Land, TX (US)

(72) Inventors: Paul E. Koppel, Hollywood, FL (US); Ravi Ravikumar, Lancaster, CA (US)

(73) Assignee: Fluor Technologies Corporation, Sugar Land, TX (US)

( * ) Notice: Subject to any disclaimer, the term of this patent is extended or adjusted under 35 U.S.C. 154(b) by 0 days.

(21) Appl. No.: 15/621,596

(22) Filed: Jun. 13, 2017

(65) Prior Publication Data

US 2017/0355911 A1    Dec. 14, 2017

Related U.S. Application Data

(60) Provisional application No. 62/349,999, filed on Jun. 14, 2016.

(51) Int. Cl.
| | |
|---|---|
| C10G 11/02 | (2006.01) |
| C07C 4/26 | (2006.01) |
| C07C 15/04 | (2006.01) |
| C07C 15/06 | (2006.01) |
| C07C 15/08 | (2006.01) |
| C10J 3/84 | (2006.01) |

(52) U.S. Cl.
CPC ........... *C10G 11/02* (2013.01); *C07C 4/26* (2013.01); *C07C 15/04* (2013.01); *C07C 15/06* (2013.01); *C07C 15/08* (2013.01); *C10J 3/84* (2013.01)

(58) Field of Classification Search
CPC .............. C10G 11/02; B01J 2219/00006
See application file for complete search history.

(56) References Cited

U.S. PATENT DOCUMENTS

| | | |
|---|---|---|
| 1,947,485 A | 2/1934 | Miller |
| 4,090,942 A | 5/1978 | Beuther et al. |
| 4,139,452 A | 2/1979 | Beuther et al. |
| 9,061,953 B2 * | 6/2015 | Johnson .............. C01B 3/34 |
| 2010/0038288 A1 | 2/2010 | Warwick et al. |
| 2010/0256428 A1 | 10/2010 | Marker et al. |
| 2011/0120138 A1 | 5/2011 | Gaiffi et al. |
| 2015/0136656 A1 * | 5/2015 | Barger .............. C10G 1/002 |
| | | 208/415 |

FOREIGN PATENT DOCUMENTS

| | | |
|---|---|---|
| CA | 3027480 A1 | 12/2017 |
| CN | 109415279 A | 3/2019 |
| IN | 201817045585 A | 2/2019 |
| WO | 2017218557 A1 | 12/2017 |

OTHER PUBLICATIONS

International Application No. PCT/US2017/037286, International Search Report and Written Opinion of the International Searching Authority, dated Sep. 29, 2017, 14 pages.
Koppel, Paul E. et al., "Processing of Gasification Tars to High Yields of BTX" filed Jun. 14, 2016, U.S. Appl. No. 62/349,999.
Foreign Communication from a Related Counterpart—International Preliminary Report on Patentability, dated Dec. 27, 2018, PCT/US2017/037286, filed on Jun. 13, 2017.

* cited by examiner

*Primary Examiner* — Randy Boyer
(74) *Attorney, Agent, or Firm* — Conley Rose, PC

(57) ABSTRACT

Embodiments relate generally to systems and method for processing tars to produce benzene, toluene, and xylene (BTX). A method for processing tars may comprise distilling the tars to separate creosotes and pitch; and processing the pitch via hydropyrolysis, including both hydrogenation and hydrocracking functions, to remove heteroatoms and break down polyaromatics in the pitch and produce monoaromatics, such as BTX. A system for processing tars may comprise one or more of the following: an input stream comprising tars feeding into a column; the column configured to separate the tars into one or more creosote streams and a pitch stream; and a reactor (or a series of reactors, or beds within a single reactor), wherein the pitch stream is fed to the reactor along with a stream of hydrogen, wherein the reactor is configured to break down the pitch to produce BTX.

19 Claims, 6 Drawing Sheets

PROCESSING OF GASIFICATION TARS TO HIGH YIELDS OF BTX

CROSS-REFERENCE TO RELATED APPLICATIONS

The present application claims priority to U.S. Provisional Patent Application Ser. No. 62/349,999 filed Jun. 14, 2016 by Paul E. Koppel, et al. and entitled "Processing of Gasification Tars to High Yields of BTX" which is incorporated herein by reference as if reproduced in its entirety.

STATEMENT REGARDING FEDERALLY SPONSORED RESEARCH OR DEVELOPMENT

Not applicable.

REFERENCE TO A MICROFICHE APPENDIX

Not applicable.

BACKGROUND

Tar is a common by-product in several well-known coal processing systems. Coal gasification and coal liquefaction both produce tars as a by-product. Additionally, tars may be produced in the form of steam cracker fuel oils, blast furnace tars, coke oven tars, and other similar highly aromatic by-products.

SUMMARY

In an embodiment, a method for processing tars may comprise distilling the tars to separate creosotes and pitch; and processing the pitch via hydropyrolysis, including both hydrogenation and hydrocracking functions, to remove heteroatoms and break down polyaromatics in the pitch and produce monoaromatics, such as benzene, toluene, and xylenes (BTX).

In an embodiment, a system for processing tars may comprise one or more of the following: an input stream comprising tars feeding into a column; the column configured to separate the tars into one or more creosote streams and a pitch stream; and a reactor (or a series of reactors, or beds within a single reactor), wherein the pitch stream is fed to the reactor along with a stream of hydrogen, wherein the reactor is configured to selectively break down the pitch to produce benzene, toluene, and xylene.

In an embodiment, a method for processing a condensed aromatic feed may comprise distilling the condensed aromatic feed to separate creosotes and pitch; processing the pitch via hydropyrolysis to remove heteroatoms and break down polyaromatics in the pitch and produce monoaromatics, such as benzene, toluene, and xylenes; distilling the output of the hydropyrolysis to separate hydrocarbon gas, benzene, toluene, p-xylene, other xylenes, hydrogen, and heavy hydrocarbons; recycling the excess hydrogen back to the hydropyrolysis process; and recycling the heavy hydrocarbons back to the hydropyrolysis process.

BRIEF DESCRIPTION OF THE DRAWINGS

For a more complete understanding of the present disclosure, reference is now made to the following brief description, taken in connection with the accompanying drawing and detailed description, wherein like reference numerals represent like parts.

DETAILED DESCRIPTION

Figure 1:
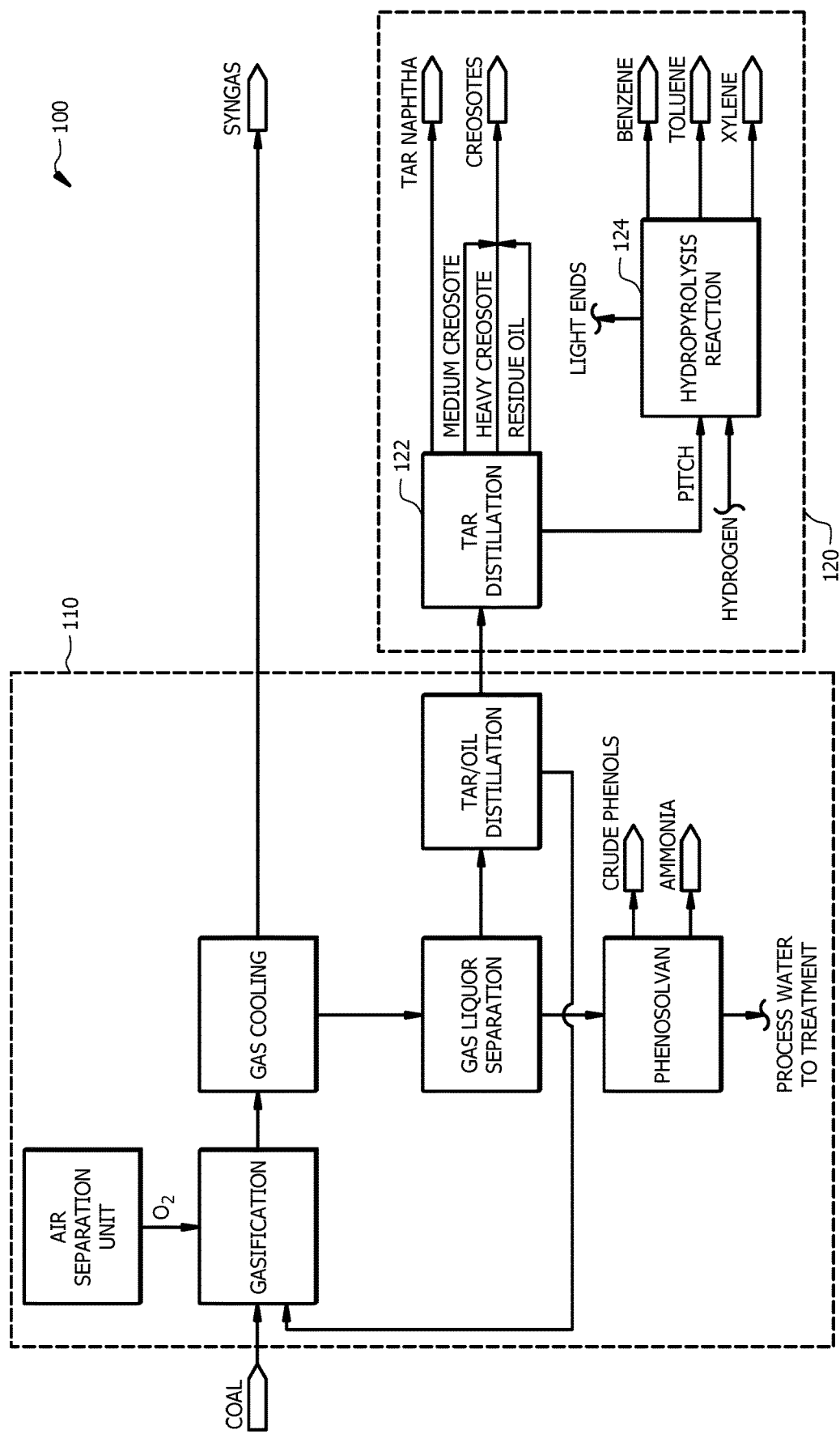
FIG. 1 illustrates a process flow diagram including a gasification process according to an embodiment of the disclosure.

It should be understood at the outset that although illustrative implementations of one or more embodiments are illustrated below, the disclosed systems and methods may be implemented using any number of techniques, whether currently known or not yet in existence. The disclosure should in no way be limited to the illustrative implementations, drawings, and techniques illustrated below, but may be modified within the scope of the appended claims along with their full scope of equivalents.

The following brief definition of terms shall apply throughout the application:

The term "comprising" means including but not limited to, and should be interpreted in the manner it is typically used in the patent context;

The phrases "in one embodiment," "according to one embodiment," and the like generally mean that the particular feature, structure, or characteristic following the phrase may be included in at least one embodiment of the present invention, and may be included in more than one embodiment of the present invention (importantly, such phrases do not necessarily refer to the same embodiment);

If the specification describes something as "exemplary" or an "example," it should be understood that refers to a non-exclusive example;

The terms "about" or "approximately" or the like, when used with a number, may mean that specific number, or alternatively, a range in proximity to the specific number, as understood by persons of skill in the art field; and If the specification states a component or feature "may," "can," "could," "should," "would," "preferably," "possibly," "typically," "optionally," "for example," "often," or "might" (or other such language) be included or have a characteristic, that particular component or feature is not required to be included or to have the characteristic. Such component or feature may be optionally included in some embodiments, or it may be excluded.

Embodiments of the disclosure include methods and systems for processing tars produced during the gasification of coal. Additionally, the methods and systems may be used to process tars produced in other processes or from other feedstocks.

Gasification of coal, particularly fixed bed systems and specifically Lurgi gasifiers, produce low value, highly aromatic tars as a by-product. Additionally, other processing systems may produce highly aromatic tars, such as steam cracker fuel oils, coal liquefaction products, blast furnace tars, coke oven tars, etc. Embodiments of the disclosure are directed toward processing these tars to maximize their economic return and methods to convert these low value liquids to high value monoaromatic chemicals.

Tars produced during gasification are currently commonly sold for low value fuel oil blending. Additionally, there are currently environmental restrictions on the use of high sulfur fuels due to the health hazards related to the current usages. While the disclosure relates to tars produced during gasification (particularly Lurgi gasification), the method of processing the tars may be applicable to any low K feedstock (where K=(mean average boiling point in degrees Rankine) $^\wedge 1/3$/specific gravity at 60° F.). For example, the disclosed processes could be carried out with tars produced from one of gasification, direct coal liquefaction, and/or steel making coke ovens.

The tars produced during gasification typically contain condensed aromatic rings. Methods of the disclosure may include using selective catalytic hydropyrolysis to break polyaromatic structures while preserving produced monoaromatics and while removing heteroatoms.

Referring now to FIG. 1, a flow diagram of a process 100 is shown, wherein the process comprises gasification of coal 110. The process 100 may comprise additional processing steps 120 of the tar produced by the gasification process 110. At step 122, the tar may be distilled to separate creosotes, naphtha, and pitch. At step 124, the pitch separated at step 122 may be processed via hydropyrolysis (including hydrogenation and hydrocracking functions) with an input of excess hydrogen to produce benzene, toluene, and xylenes (BTX). The hydropyrolysis reaction 124 may also be called the hydropyrolysis process 124, as it includes hydrogenation and hydrocracking functions.

In some embodiments, the hydropyrolysis process 124 may comprise the use of a catalyst. In some embodiments, the catalyst may comprise one or more of the following: nickel, cobalt, molybdenum tungsten, phosphorous, and/or one or more support materials.

Excess hydrogen may be kept sufficiently high during the hydropyrolysis process 124 to avoid excessive coke deposition on the catalyst. Depending on the contents of the feed, the hydropyrolysis process could be carried out in one of a fixed bed reactor(s), an ebullated bed reactor, bubble column, and/or a circulating bed arrangement.

In some embodiments, the operating pressure of the hydropyrolysis process 124 may be between approximately 600-1800 psi. In some embodiments, the operating pressure of the hydropyrolysis process 124 may be between approximately 500-2500 psi. In some embodiments, the operating temperature of the hydropyrolysis 124 may be between approximately 650-850° F. In some embodiments, the operating temperature of the hydropyrolysis process 124 may be between approximately 680-790° F. In some embodiments, the operating temperature of the hydropyrolysis process 124 may be approximately 750° F. The operating conditions may constitute "mild" conditions configured to break the pitch down to BTX without destroying the structure of the monoaromatics.

In some embodiments, the yields of BTX targeted from the hydropyrolysis process 124 may be at least 50%. In some embodiments, the yields of BTX targeted from the hydropyrolysis process 124 may be higher than approximately 70%. In some embodiments, the yields of BTX targeted from the hydropyrolysis process 124 may be approximately 90%. The yields of BTX from the process 120 may be highly dependent on feedstock characterization and reaction operating conditions. In some embodiments, the remaining liquid yield may be in the low sulfur atmospheric distillate range.

Typically, the tar and pitch products of these processes are difficult to manage, as they are unstable, and create issues with storage and emissions. By further processing the tar and pitch products, the disclosed methods may produce more valuable and useful products (as BTX) that are more easily stored and transported.

Figure 2:
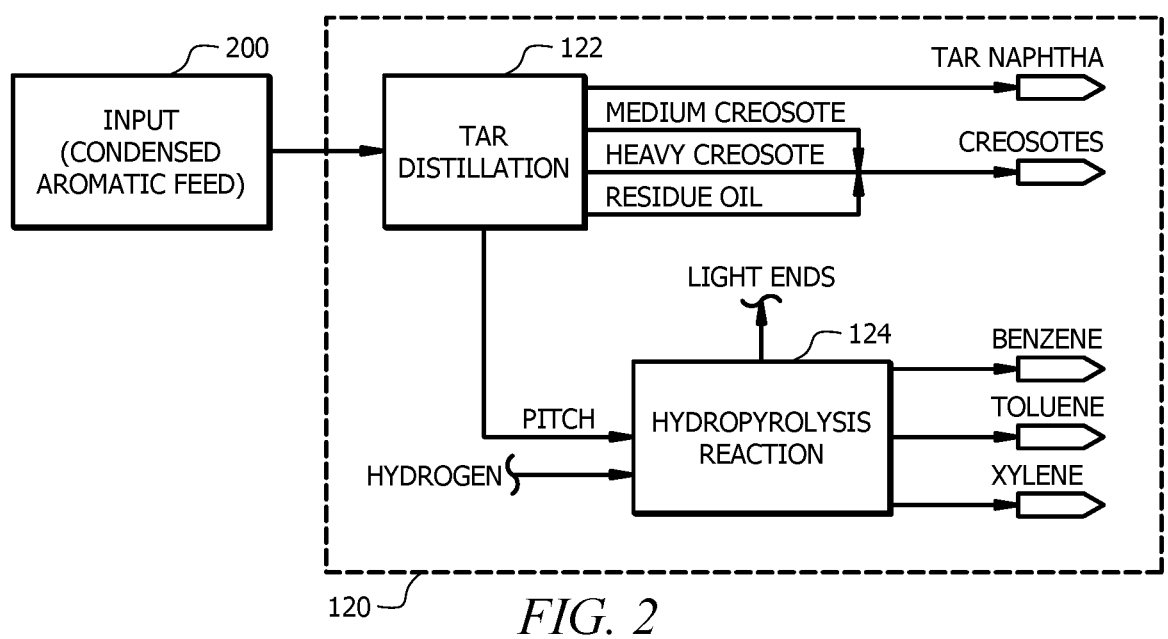
FIG. 2 illustrates a process flow diagram comprising a hydropyrolysis reaction, according to an embodiment of the disclosure.

FIG. 2 illustrates a more detailed view of the additional processing steps 120 described above, where the input 200 to the additional processing steps 120 may be any source of tar. The system 100 described in FIG. 1 may comprise one example of a tar input 200 to the additional processing steps 120. The input 200 to the additional processing steps 120 may comprise a condensed aromatic feed stock, which may comprise a coal liquid feed stock. The input 200 may comprise products from one or a combination of the following: a coal gasification process, a direct coal liquefaction process, steam cracking pyrolysis fuel oil, and steel making coke ovens. Additionally, the input 200 may comprise products from any process or storage as long as the input 200 comprises condensed aromatics.

Figure 3:
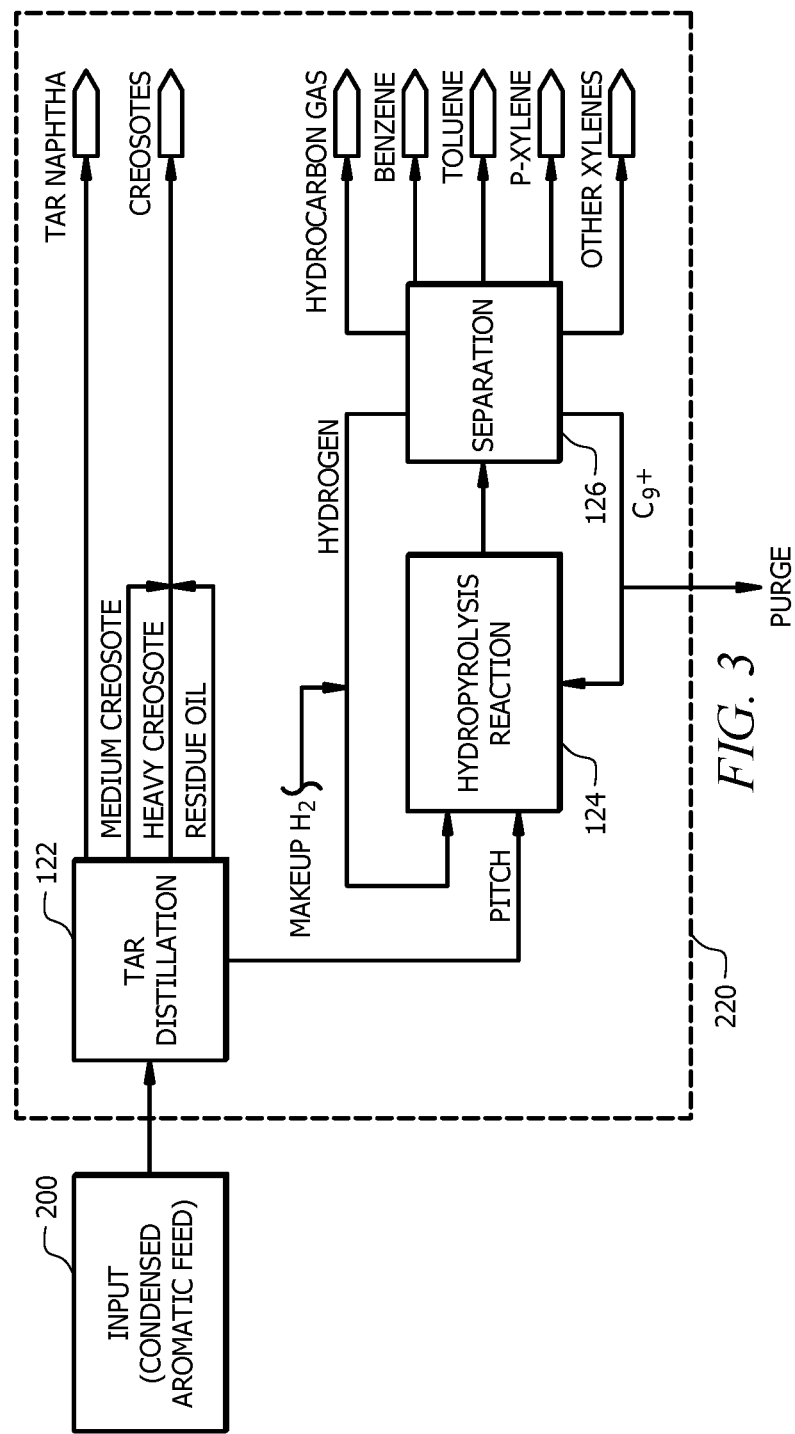
FIG. 3 illustrates another process flow diagram comprising a hydropyrolysis reaction, according to an embodiment of the disclosure.

FIG. 3 illustrates another embodiment of the additional processing steps 220, where the pitch from the tar distillation 122 may be processed by a hydropyrolysis process 124, as described above. Additionally, the output stream from the hydropyrolysis process 124 may be fed to a system of separation columns 126, where the output stream may be separated into hydrocarbon gas, benzene, toluene, p-xylene, other xylenes, hydrogen, and heavy hydrocarbons (such as $C_{9+}$). The hydrogen may be recycled back to the hydropyrolysis process 124 to provide excess hydrogen to the reaction. The heavy hydrocarbons may also be recycled back to the hydropyrolysis process 124, and in some embodiments, a portion of the recycle stream of the heavy hydrocarbons may be purged, to prevent build-up in the reaction.

The system 100 described in FIG. 1 may comprise one example of a tar input 200 to the additional processing steps 220. The input 200 to the additional processing steps 220 may comprise a condensed aromatic feed stock, which may comprise a coal liquid feed stock. The input 200 may comprise products from one or a combination of the following: a coal gasification process, a direct coal liquefaction process, and steel making coke ovens. Additionally, the input 200 may comprise products from any process or storage as long as the input 200 comprises condensed aromatics.

Figure 4:
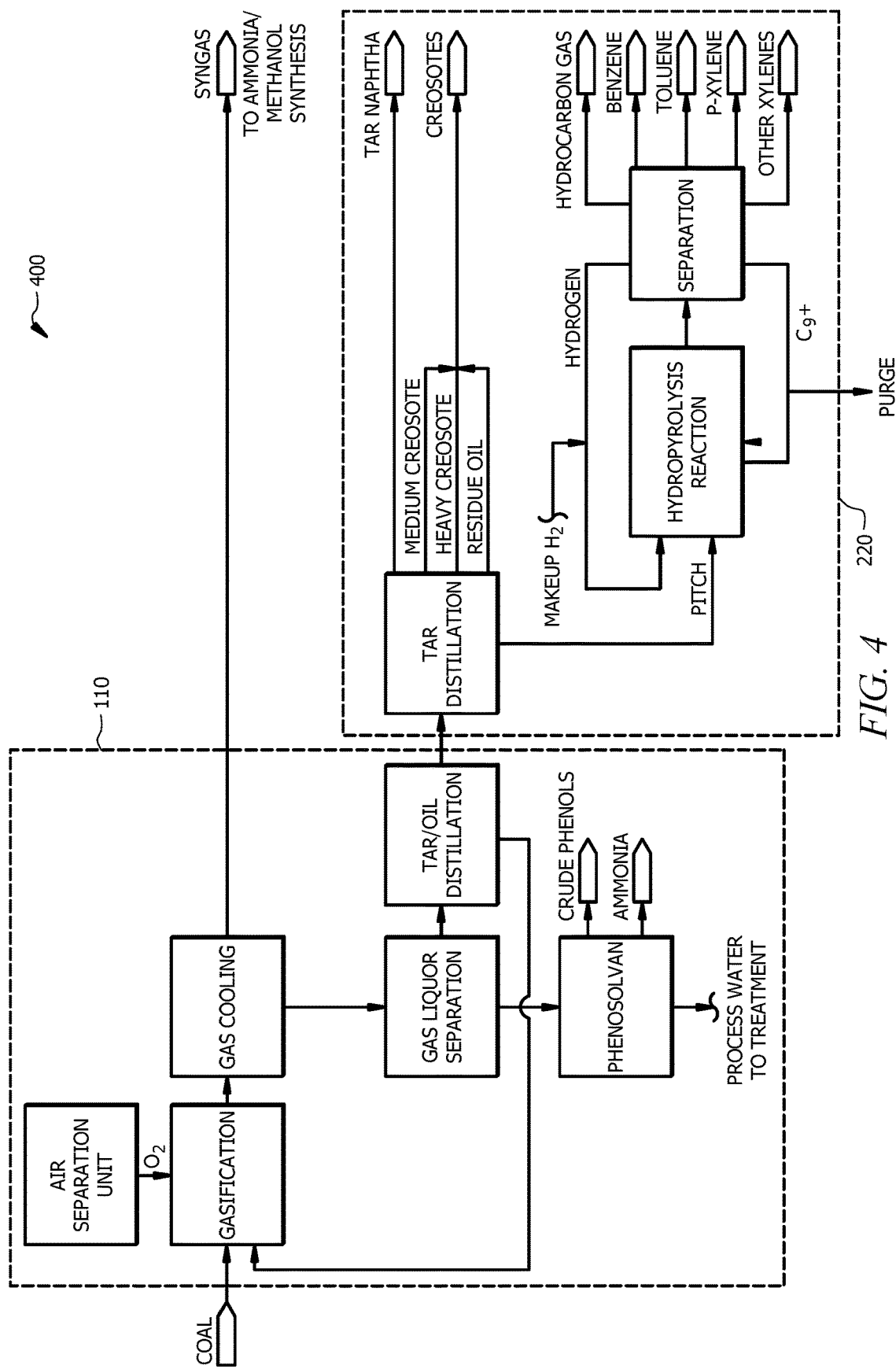
FIG. 4 illustrates another process flow diagram including a gasification process according to an embodiment of the disclosure.

FIG. 4 illustrates another embodiment of an overall processing system 400 comprising, where the coal gasification process 110 first described in FIG. 1 may provide the input for the additional processing steps 220. FIG. 4 illustrates one example of how the additional processing steps 220 may be implemented with an existing source of a highly aromatic feed.

Figure 5:
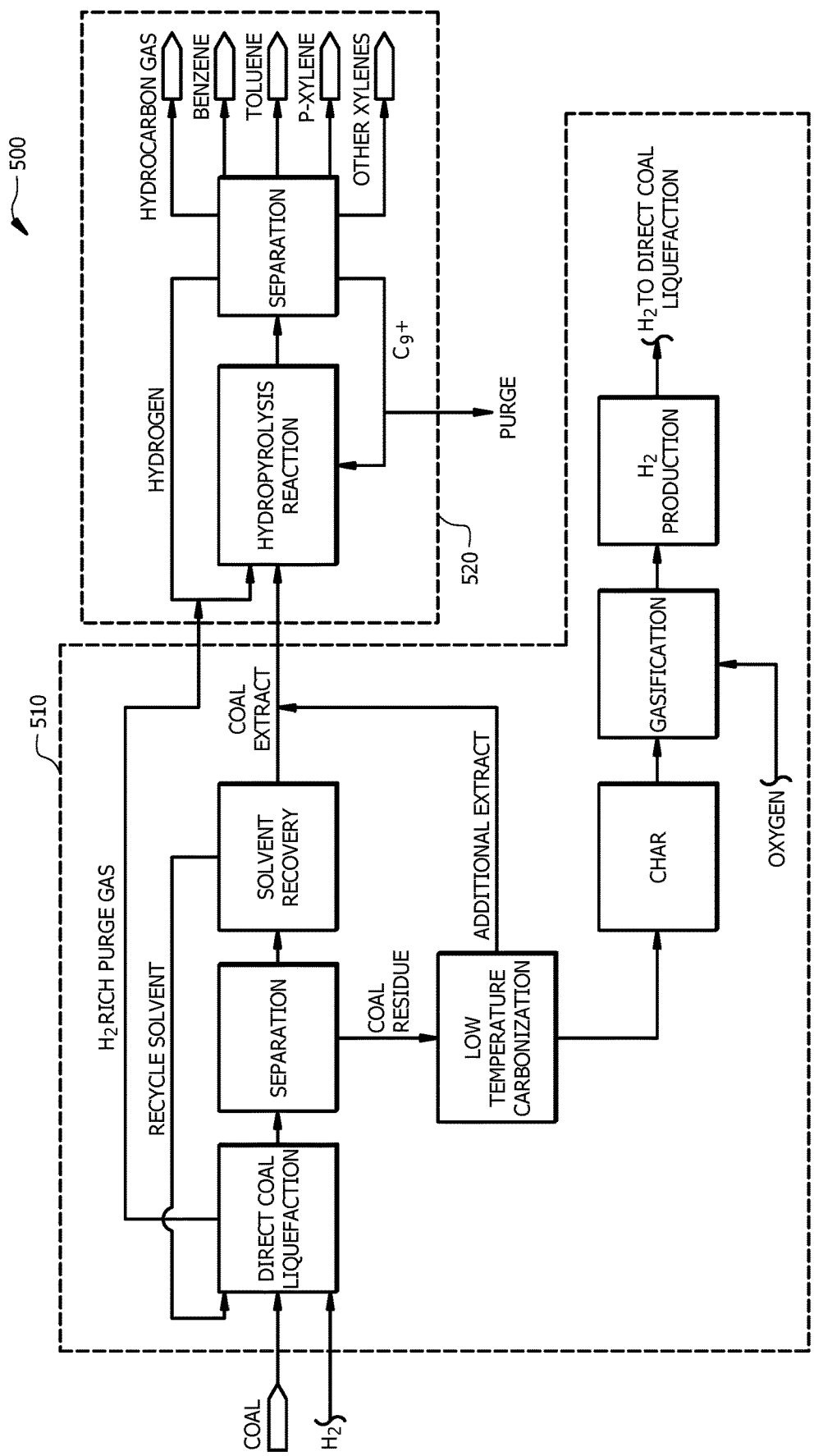
FIG. 5 illustrates a process flow diagram including a coal liquefaction process according to an embodiment of the disclosure.

FIG. 5 illustrates another example of an overall processing system 500, wherein the input to the additional processing steps 520 comprises direct coal liquefaction 510. The additional processing steps 520 may be similar to the additional processing steps 220 described in FIG. 3, where the tar distillation 122 step may be incorporated into the separation step in the direct coal liquefaction 510. The direct coal liquefaction process may use hydrogen and recycle solvent at approximately 1500 to 2500 psig pressure, yielding coal extract and coal residue. The liquefaction reactor product may be routed to a separation unit to separate extract/solvent from residue. The extract/solvent portion may be further processed to recover solvent for the recycle of coal hydrogenation. The separated coal extract may be similar to the pitch produced from the tar distillation step described above. Optionally, the coal extract may be fed to a tar distillation unit for creosote recovery, similar to the additional processing steps 220 described above. The coal extract may then be hydro-pyrolysed and fed to a separator to yield BTX (similar to the hydropyrolysis described above in FIG. 3). The coal residue may be further processed to recover lighter coal extract with the balance converted to char that is gasified to produce $H_2$ required for direct coal liquefaction and hydropyrolysis.

Figure 6:
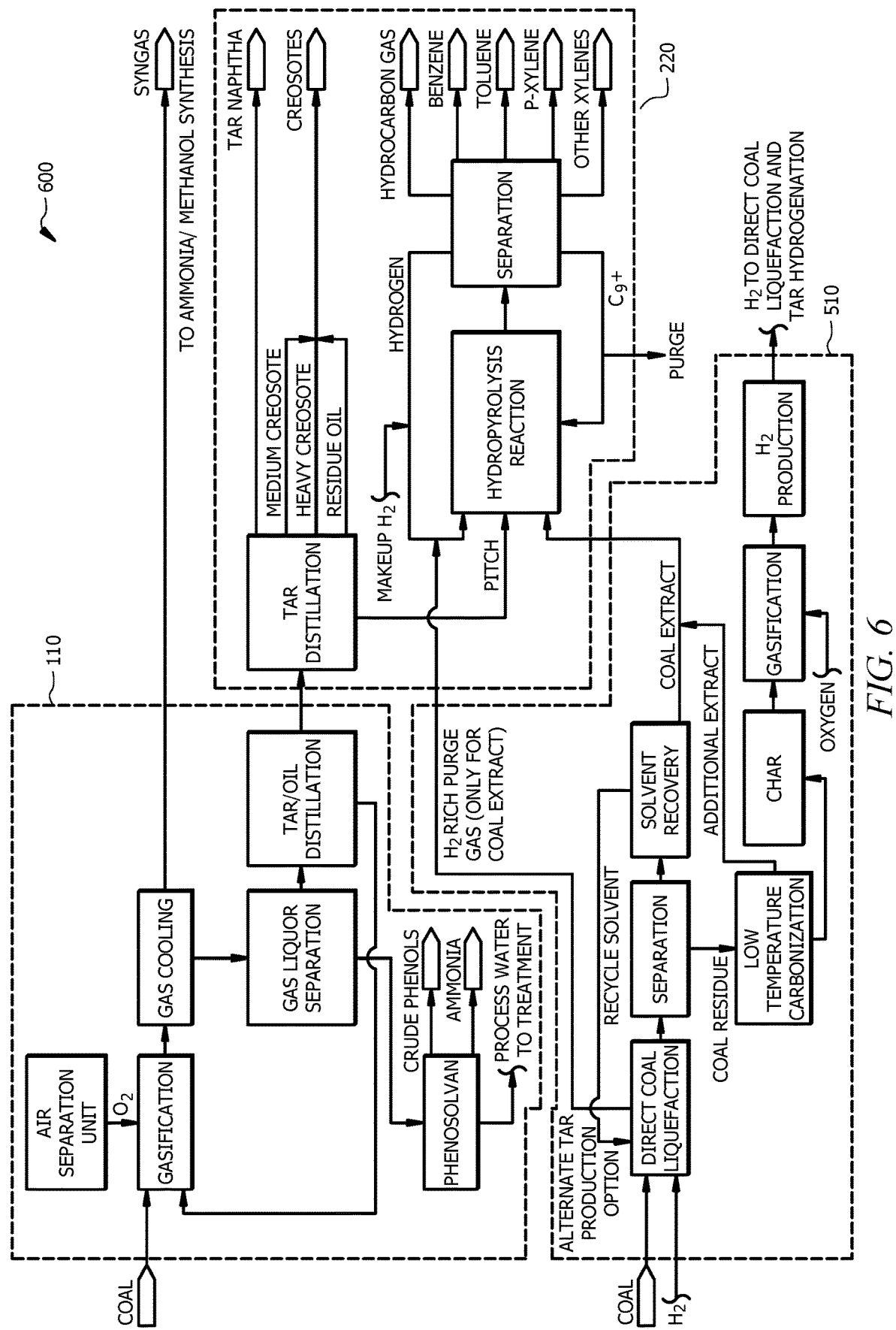
FIG. 6 illustrates a process flow diagram including a gasification process and a liquefaction process according to an embodiment of the disclosure.

FIG. 6 illustrates yet another example of an overall processing system 600, where a combination of multiple tar sources are input to the additional processing steps 220. In FIG. 6, the coal gasification process 110 and coal liquefaction process 510 may both send inputs to the additional processing system 220. Both processes 110 and 510 may function as described above. Optionally, excess hydrogen purge gas may be fed from the direct coal liquefaction to be combined with the recycled hydrogen stream into the hydropyrolysis reaction.

FIGS. 1, 4, 5, and 6 illustrate exemplary processes for producing a highly aromatic feed to the additional processing steps, but alternative processes may also produce highly aromatic feeds that may be processed by the additional processing steps to produce BTX.

Embodiments of the disclosure comprise a method for processing tars comprising one or more of the following steps: distilling the tars to separate creosotes and pitch; and processing the pitch via hydropyrolysis (including both hydrogenation and hydrocracking functions) to remove heteroatoms and break down polyaromatics in the pitch and produce monoaromatics (such as benzene, toluene, and xylenes).

In an embodiment of the method, processing comprises catalytically hydropyrolyzing the pitch. In an embodiment of the method, hydropyrolyzing yields BTX at a concentration of at least 50%. In an embodiment of the method, the method further comprises monitoring the presence of hydrogen in a hydropyrolysis unit. In an embodiment of the method, the method further comprises conveying pitch from the distillation unit to the hydropyrolysis unit. In an embodiment of the method, the method may further comprise one or more of the following steps: gasification of coal; cooling the gas; separating the liquid from the gas; separating the tar and oil; distilling and separating the tar and oil; feeding the oil back to the gasification of the coal; and feeding the tar into a distillation column.

In an embodiment of the method, the operating pressure of the hydropyrolysis is between approximately 600-1800 psi. In an embodiment of the method, the operating pressure of the hydropyrolysis is between approximately 500-2500 psi. In an embodiment of the method, the operating temperature of the hydropyrolysis is between approximately 650-850° F. In an embodiment of the method, the operating temperature of the hydropyrolysis is between approximately 680-790° F. In an embodiment of the method, the operating temperature of the hydropyrolysis is approximately 750° F. In an embodiment of the method, the tars are products of a coal gasification process. In an embodiment of the method, the tars are products of a direct coal liquefaction process. In an embodiment of the method, the tars are products of steel making coke ovens. In an embodiment of the method, the tars are products of gas oil steam cracking, or any other chemically suitable low K polyaromatic feed. In an embodiment of the method, the hydropyrolysis processing comprises the use of a catalyst. In an embodiment of the method, the catalyst comprises one or more of the following materials: nickel, cobalt, molybdenum tungsten, phosphorous, and/or one or more support materials.

Embodiments of the disclosure include a system for processing tars comprising: an input stream comprising tars feeding into a column; the column configured to separate the tars into one or more creosote streams and a pitch stream; and a reactor or series of reactors or beds within a single reactor, wherein the pitch stream is fed to the reactor along with a stream of hydrogen or hydrogen rich gas, wherein the reactor is configured to break down the pitch to produce benzene, toluene, and xylenes.

In an embodiment of the system, the reactor completes hydropyrolysis of the pitch. In an embodiment of the system, input stream is a product of a coal gasification process. In an embodiment of the system, input stream is a product of a direct coal liquefaction process. In an embodiment of the system, input stream is a product of steel making coke ovens. In an embodiment of the method, the tars are products of gas oil steam cracking, or any other chemically suitable low K polyaromatic feed. In an embodiment of the system, the reactor operates at a temperature of approximately 750° F.

Having described various devices and methods herein, exemplary embodiments or aspects can include, but are not limited to:

In a first embodiment, a method for processing tars may comprise distilling the tars to separate creosotes and pitch; and processing the pitch via hydropyrolysis, including both hydrogenation and hydrocracking functions, to remove heteroatoms and break down polyaromatics in the pitch and produce monoaromatics, such as benzene, toluene, and xylenes.

A second embodiment can include the method of the first embodiment, wherein processing comprises catalytically hydropyrolyzing the pitch.

A third embodiment can include the method of the first or second embodiments, wherein hydropyrolyzing yields BTX at a concentration of at least 50%.

A fourth embodiment can include the method of any of the first to third embodiments, further comprising monitoring the presence of hydrogen in a hydropyrolysis unit.

A fifth embodiment can include the method of any of the first to fourth embodiments, further comprising conveying pitch from the distillation unit to the hydropyrolysis unit.

A sixth embodiment can include the method of any of the first to fifth embodiments, further comprising, after processing the pitch via hydropyrolysis, distilling the output of the hydropyrolysis to separate hydrocarbon gas, benzene, toluene, p-xylene, other xylenes, hydrogen, and heavy hydrocarbons; recycling the excess hydrogen back to the hydropyrolysis process; and recycling the heavy hydrocarbons back to the hydropyrolysis process.

A seventh embodiment can include method of the sixth embodiment, further comprising purging at least a portion of the heavy hydrocarbons off of the recycle stream.

An eighth embodiment can include the method of any of the first to seventh embodiments, wherein the operating pressure of the hydropyrolysis process is between approximately 500-2500 psi.

A ninth embodiment can include the method of any of the first to eighth embodiments, wherein the operating temperature of the hydropyrolysis process is approximately 750° F.

A tenth embodiment can include the method of any of the first to ninth embodiments, wherein the tars are products of one or more of a coal gasification process, a direct coal liquefaction process, steel making coke ovens, and gas oil steam cracking.

An eleventh embodiment can include the method of any of the first to tenth embodiments, wherein the hydropyrolysis processing comprises the use of a catalyst.

A twelfth embodiment can include the method of any of the first to eleventh embodiments, wherein the catalyst comprises one or more of the following materials: nickel, cobalt, molybdenum tungsten, phosphorous, and/or one or more support materials.

A thirteenth embodiment can include the method of any of the first to twelfth embodiments, further comprising, before distilling the tars, gasifying of coal; cooling the gas; separating liquid from the gas; separating the tar and oil; distilling and separating the tar and oil; feeding the oil back to the gasification of the coal; and feeding the tar into a distillation column.

A fourteenth embodiment can include the method of any of the first to thirteenth embodiments, further comprising, before processing the pitch via hydropyrolysis, liquefaction of coal; separation of coal residue; recovery of solvent; recycling the recovered solvent to the liquefaction of coal; feeding the coal extract from the solvent recovery to the hydropyrolysis processing; and feeding a hydrogen rich purge gas from the liquefaction of coal to the hydropyrolysis processing.

In a fifteenth embodiment, a system for processing tars may comprise one or more of the following: an input stream comprising tars feeding into a column; the column configured to separate the tars into one or more creosote streams and a pitch stream; and a reactor (or a series of reactors, or beds within a single reactor), wherein the pitch stream is fed to the reactor along with a stream of hydrogen, wherein the reactor is configured to break down the pitch to produce benzene, toluene, and xylene.

A sixteenth embodiment can include the system of the fifteenth embodiment, wherein the reactor completes hydropyrolysis of the pitch.

A seventeenth embodiment can include the system of the fifteenth or sixteenth embodiments, wherein the reactor produces an output stream comprising the benzene, toluene, and xylene, and the system further comprising a second column configured to separate the output stream into at least a benzene stream, a toluene stream, and at least one xylene stream.

An eighteenth embodiment can include the system of any of the fifteenth to seventeenth embodiments, wherein the input stream is produced via one or more of the following: a coal gasification process, a direct coal liquefaction process, steel making coke ovens, and gas oil steam cracking.

In a nineteenth embodiment, a method for processing a condensed aromatic feed may comprise distilling the condensed aromatic feed to separate creosotes and pitch; processing the pitch via hydropyrolysis to remove heteroatoms and break down polyaromatics in the pitch and produce monoaromatics, such as benzene, toluene, and xylenes; distilling the output of the hydropyrolysis process to separate hydrocarbon gas, benzene, toluene, p-xylene, other xylenes, hydrogen, and heavy hydrocarbons; recycling the excess hydrogen back to the hydropyrolysis process; and recycling the heavy hydrocarbons back to the hydropyrolysis process.

A twentieth embodiment can include the method of the nineteenth embodiment, wherein the operating pressure of the hydropyrolysis process is between approximately 500-2500 psi.

While various embodiments in accordance with the principles disclosed herein have been shown and described above, modifications thereof may be made by one skilled in the art without departing from the spirit and the teachings of the disclosure. The embodiments described herein are representative only and are not intended to be limiting. Many variations, combinations, and modifications are possible and are within the scope of the disclosure. Alternative embodiments that result from combining, integrating, and/or omitting features of the embodiment(s) are also within the scope of the disclosure. Accordingly, the scope of protection is not limited by the description set out above, but is defined by the claims which follow that scope including all equivalents of the subject matter of the claims. Each and every claim is incorporated as further disclosure into the specification, and the claims are embodiment(s) of the present invention(s). Furthermore, any advantages and features described above may relate to specific embodiments but shall not limit the application of such issued claims to processes and structures accomplishing any or all of the above advantages or having any or all of the above features.

Additionally, the section headings used herein are provided for consistency with the suggestions under 37 C.F.R. 1.77 or to otherwise provide organizational cues. These headings shall not limit or characterize the invention(s) set out in any claims that may issue from this disclosure. Specifically and by way of example, although the headings might refer to a "Field," the claims should not be limited by the language chosen under this heading to describe the so-called field. Further, a description of a technology in the "Background" is not to be construed as an admission that certain technology is prior art to any invention(s) in this disclosure. Neither is the "Summary" to be considered as a limiting characterization of the invention(s) set forth in issued claims. Furthermore, any reference in this disclosure to "invention" in the singular should not be used to argue that there is only a single point of novelty in this disclosure. Multiple inventions may be set forth according to the limitations of the multiple claims issuing from this disclosure, and such claims accordingly define the invention(s), and their equivalents, that are protected thereby. In all instances, the scope of the claims shall be considered on their own merits in light of this disclosure, but should not be constrained by the headings set forth herein.

Use of broader terms such as "comprises," "includes," and "having" should be understood to provide support for narrower terms such as "consisting of," "consisting essentially of," and "comprised substantially of." Use of the terms "optionally," "may," "might," "possibly," and the like with respect to any element of an embodiment means that the element is not required, or alternatively, the element is required, both alternatives being within the scope of the embodiment(s). Also, references to examples are merely provided for illustrative purposes, and are not intended to be exclusive.

While several embodiments have been provided in the present disclosure, it should be understood that the disclosed systems and methods may be embodied in many other specific forms without departing from the spirit or scope of the present disclosure. The present examples are to be considered as illustrative and not restrictive, and the intention is not to be limited to the details given herein. For example, the various elements or components may be combined or integrated in another system, or certain features may be omitted or not implemented.

Also, techniques, systems, subsystems, and methods described and illustrated in the various embodiments as discrete or separate may be combined or integrated with other systems, modules, techniques, or methods without departing from the scope of the present disclosure. Other items shown or discussed as directly coupled or communicating with each other may be indirectly coupled or communicating through some interface, device, or intermediate component, whether electrically, mechanically, or otherwise. Other examples of changes, substitutions, and alterations are ascertainable by one skilled in the art and could be made without departing from the spirit and scope disclosed herein.

What is claimed is:

1. A method for processing tars, the method comprising:
gasifying coal to produce a gas;
cooling the gas;
separating a liquid from the gas;
separating tar and oil from the liquid;
distilling and separating the tar and the oil;
feeding the oil back to the gasification of the coal; and
feeding the tar into a distillation column;
distilling the tars in the distillation column to separate creosotes and pitch;
processing the pitch with an excess of hydrogen via a hydropyrolysis reaction, including both hydrogenation and hydrocracking functions, to remove heteroatoms and break down polyaromatics in the pitch, wherein the hydropyrolysis reaction occurs in one of a fixed bed reactor, an ebullated bed reactor, a bubble column, or a circulating bed reactor;
producing, via the hydropyrolysis of the pitch with the excess of hydrogen, monoaromatics comprising benzene, toluene, and xylenes (BTX) at a concentration of at least 50%;
distilling the output of the hydropyrolysis process to separate hydrocarbon gas, benzene, toluene, p-xylene, other xylenes, hydrogen, and heavy hydrocarbons;
recycling the excess hydrogen back to the hydropyrolysis process; and
recycling the heavy hydrocarbons back to the hydropyrolysis process.

2. The method of claim 1, wherein processing comprises catalytically hydropyrolyzing the pitch.

3. The method of claim 1, further comprising: monitoring the presence of hydrogen in a hydropyrolysis unit.

4. The method of claim 1, further comprising: conveying pitch from the distillation unit to the hydropyrolysis unit.

5. The method of claim 1, further comprising: purging at least a portion of the heavy hydrocarbons off of the recycle stream.

6. The method of claim 1, wherein the operating pressure of the hydropyrolysis process is between approximately 500-2500 psi.

7. The method of claim 1, wherein the operating temperature of the hydropyrolysis process is approximately 750° F.

8. The method of claim 1, wherein the tars are products of one or more of a coal gasification process, a direct coal liquefaction process, steel making coke ovens, or gas oil steam cracking.

9. The method of claim 1, wherein the hydropyrolysis processing comprises the use of a catalyst.

10. The method of claim 9, wherein the catalyst comprises one or more of the following materials: nickel, cobalt, molybdenum tungsten, or phosphorous, and one or more support materials.

11. A method for processing tars and coal extract, the method comprising:
liquefying coal to produce a liquefaction product;
separating a coal residue from the liquefaction product;
recovering solvent and a coal extract from the coal residue;
recycling the recovered solvent to the liquefaction of coal;
feeding the coal extract from the solvent recovery to a hydropyrolysis process;
distilling the tars to separate creosotes and pitch;
feeding a hydrogen rich purge gas from the liquefaction of coal to the hydropyrolysis process;
processing the pitch and the coal extract with an excess of hydrogen via a hydropyrolysis reaction, including both hydrogenation and hydrocracking functions, to remove heteroatoms and break down polyaromatics in the pitch;
producing, via the hydropyrolysis of the pitch and the coal extract with the excess of hydrogen, monoaromatics comprising benzene, toluene, and xylenes (BTX) at a concentration of at least 50%;
distilling the output of the hydropyrolysis process to separate hydrocarbon gas, benzene, toluene, p-xylene, other xylenes, hydrogen, and heavy hydrocarbons;
recycling the excess hydrogen back to the hydropyrolysis process; and
recycling the heavy hydrocarbons back to the hydropyrolysis process.

12. A system for processing tars comprising:
a gasifier configured to gasifying coal to produce a gas;
a cooler configured to receive and cool the gas;
a first separator configured to separate a liquid from the gas;
a second separator configured to receive the liquid from the first separator and separate tars and oil from the liquid;
a distillation system configured to distill and separate the tars from the oil, wherein the system is configured to pass the oil to the gasifier, and wherein the system is configured to pass the tars to a column;
the column, wherein the column comprises the tars from the liquid, wherein the column is configured to separate the tars into one or more creosote streams and a pitch stream; and
a reactor in fluid communication with the column, wherein the reactor is configured to receive the pitch stream along with a stream of hydrogen, and wherein the reactor is configured to selectively break down the pitch to produce benzene, toluene, and xylene.

13. The system of claim 12, wherein the reactor is configured to complete hydropyrolysis of the pitch.

14. The system of claim 12, wherein the reactor is configured to produce an output stream comprising the benzene, toluene, and xylene, and the system further comprising a second column configured to separate the output stream from the reactor into at least a benzene stream, a toluene stream, and at least one xylene stream.

15. The system of claim 14, further comprising an initial process configured to produce the input stream, wherein the initial process is configured to perform a coal gasification process, a direct coal liquefaction process, steel making coke ovens, or gas oil steam cracking.

16. A method for processing a condensed aromatic feed, the method comprising:
liquefying coal to produce a liquefaction product;
separating a coal residue from the liquefaction product;
recovering solvent and a coal extract from the coal residue;
recycling the recovered solvent to the liquefaction of coal;

feeding the coal extract from the solvent recovery to a tar distillation process;

distilling the coal extract to separate creosotes and pitch;

processing the pitch via hydropyrolysis to remove heteroatoms and break down polyaromatics in the pitch;

producing monoaromatics comprising benzene, toluene, and xylenes;

distilling the output of the hydropyrolysis process to separate hydrocarbon gas, benzene, toluene, p-xylene, other xylenes, hydrogen, and heavy hydrocarbons;

recycling the excess hydrogen back to the hydropyrolysis process; and recycling the heavy hydrocarbons back to the hydropyrolysis process.

17. The method of claim 16, wherein the operating pressure of the hydropyrolysis process is between approximately 500-2500 psi.

18. The method of claim 16, wherein processing the pitch comprises processing the pitch with an excess of hydrogen, and wherein producing the monoaromatics comprises producing the monoaromatics at a concentration of at least 50%.

19. The system of claim 14, wherein the second column is further configured to separate the output stream from the reactor into an additional hydrogen stream and a heavy hydrocarbons stream; recycle the excess hydrogen back to the reactor; and recycle the heavy hydrocarbons back to the reactor.

* * * * *